United States Patent

Bryant et al.

[11] Patent Number: 5,958,916
[45] Date of Patent: Sep. 28, 1999

[54] DIHYDRONAPHTHALENE AND NAPHTHALENE COMPOUNDS, INTERMEDIATES, FORMULATIONS, AND METHODS

[75] Inventors: Henry Uhlman Bryant; Thomas Alan Crowell; Charles David Jones, all of Indianapolis, Ind.

[73] Assignee: Eli Lilly and Company, Indianapolis, Ind.

[21] Appl. No.: 08/918,479

[22] Filed: Aug. 26, 1997

Related U.S. Application Data

[60] Provisional application No. 60/024,201, Aug. 29, 1996.

[51] Int. Cl.[6] .................. A61K 31/135; A61K 31/445; C07C 225/10; C07D 211/34
[52] U.S. Cl. .................. 514/212; 514/239.2; 514/319; 514/428; 514/648; 540/609; 544/174; 546/205; 546/206; 548/571; 564/324
[58] Field of Search .................. 564/324; 548/571; 546/205, 206; 544/174; 540/609; 514/212, 239.2, 319, 428, 648

[56] References Cited

U.S. PATENT DOCUMENTS

| | | | |
|---|---|---|---|
| 3,394,125 | 7/1968 | Crenshaw | 548/525 |
| 3,413,305 | 11/1968 | Crenshaw | 548/525 |
| 4,133,814 | 1/1979 | Jones et al. | |
| 4,230,862 | 10/1980 | Suarez et al. | 546/237 |
| 4,323,707 | 4/1982 | Suarez et al. | 564/324 |
| 4,358,593 | 11/1982 | Jones et al. | 546/202 |
| 4,380,635 | 4/1983 | Peters | |
| 4,418,068 | 11/1983 | Jones et al. | 546/237 |
| 5,395,842 | 3/1995 | Labrie | 514/320 |
| 5,470,854 | 11/1995 | Angerer et al. | 514/233 |
| 5,472,962 | 12/1995 | Koizumi et al. | 514/233.5 |
| 5,484,795 | 1/1996 | Bryant et al. | 514/319 |

FOREIGN PATENT DOCUMENTS

| | | |
|---|---|---|
| 062 503 | 10/1982 | European Pat. Off. |
| WO 89/0289 | 4/1989 | WIPO |
| WO 95/10513 | 4/1995 | WIPO |

OTHER PUBLICATIONS

Crenshaw, R.R., et al, *J. Med. Chem.* 14(12):1185–1190 (1971).
Jones, C.D., et al, *J. Med. Chem. 27:* 1057–1066) 1984.
Jones, C.D., et al, *J. Med. Chem. 35:* 931–938 1992.

*Primary Examiner*—Richard L. Raymond
*Attorney, Agent, or Firm*—Gilbert T. Voy

[57] ABSTRACT

The instant invention provides dihydronaphthalene and naphthalene compounds, intermediates, formulations, and methods for use in the treatment of bone loss or bone resorption.

9 Claims, No Drawings

DIHYDRONAPHTHALENE AND NAPHTHALENE COMPOUNDS, INTERMEDIATES, FORMULATIONS, AND METHODS

This application claims benefit of Provisional Application No. 60/024,201, filed Aug. 29, 1996.

BACKGROUND OF THE INVENTION

This invention relates to the field of pharmaceutical and organic chemistry and provides dihydronaphthalene or naphthalene compounds, intermediates, formulations, and methods.

Osteoporosis describes a group of diseases which arises from diverse etiologies, but which are characterized by the net loss of bone mass per unit volume. The consequence of this loss of bone mass and resulting bone fracture is the failure of the skeleton to provide adequate support for the body. One of the most common types of osteoporosis is associated with menopause. Most women lose from about 20% to about 60% of the bone mass in the trabecular compartment of the bone within 3 to 6 years after the cessation of menses. This rapid loss is generally associated with an increase of bone resorption and formation. However, the resorptive cycle is more dominant and the result is a net loss of bone mass. Osteoporosis is a common and serious disease among postmenopausal women.

There are an estimated 25 million women in the United States alone who are afflicted with this disease. The results of osteoporosis are personally harmful, and also account for a large economic loss due to its chronicity and the need for extensive and long term support (hospitalization and nursing home care) from the disease sequelae. This is especially true in more elderly patients. Additionally, although osteoporosis is generally not thought of as a life threatening condition, a 20% to 30% mortality rate is related to hip fractures in elderly women. A large percentage of this mortality rate can be directly associated with postmenopausal osteoporosis.

The most generally accepted method for the treatment of postmenopausal osteoporosis is estrogen replacement therapy. Although therapy is generally successful, patient compliance with the therapy is low, primarily because estrogen treatment frequently produces undesirable side effects. An additional method of treatment would be the administration of a bisphosphonate compound, such as, for example, Fosomax® (Merck & Co., Inc.).

Throughout premenopausal time, most women have less incidence of cardiovascular disease than men of the same age. Following menopause, however, the rate of cardiovascular disease in women slowly increases to match the rate seen in men. This loss of protection has been linked to the loss of estrogen and, in particular, to the loss of estrogen's ability to regulate the levels of serum lipids. The nature of estrogen's ability to regulate serum lipids is not well understood, but evidence to date indicates that estrogen can up regulate the low density lipid (LDL) receptors in the liver to remove excess cholesterol. Additionally, estrogen appears to have some effect on the biosynthesis of cholesterol, and other beneficial effects on cardiovascular health.

It has been reported in the literature that serum lipid levels in postmenopausal women having estrogen replacement therapy return to concentrations found in the premenopausal state. Thus, estrogen would appear to be a reasonable treatment for this condition. However, the side effects of estrogen replacement therapy are not acceptable to many women, thus limiting the use of this therapy. An ideal therapy for this condition would be an agent which regulates serum lipid levels in a manner analogous to estrogen, but which is devoid of the side effects and risks associated with estrogen therapy.

Thus, it would be a significant contribution to the art to provide novel compounds useful, for example, in the treatment or prevention of the disease states as indicated herein.

SUMMARY OF THE INVENTION

The instant invention relates to compounds of formula I

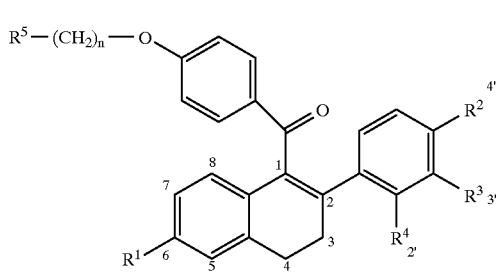

wherein
  $R^1$ is —H, —OH, —O($C_1$-$C_4$ alkyl), —OCO($C_1$-$C_6$ alkyl), —O—CO—O($C_1$-$C_6$ alkyl), —O—CO—Ar, —OSO$_2$($C_2$-$C_6$ alkyl), —O—CO—OAr, where Ar is optionally substituted phenyl;
  $R^2$ is —H, —Cl, —F, $C_1$-$C_4$ alkyl, —OH, —O($C_1$-$C_4$ alkyl), —OCO($C_1$-$C_6$ alkyl), —O—CO—O($C_1$-$C_6$ alkyl), —O—CO—Ar, —OSO$_2$($C_2$-$C_6$ alkyl), or —O—CO—OAr, where Ar is optionally substituted phenyl;
  $R^3$ and $R^4$ are, independently, $R^2$, with the proviso that $R^3$ and $R^4$ are not both hydrogen;
  $R^5$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino; and
  n is 2 or 3;
or a pharmaceutically acceptable salt or solvate thereof.

DETAILED DESCRIPTION

Also provided by the present invention are intermediate compounds of formula IIA and IIB which are useful for preparing the pharmaceutically active compounds of the present invention, and are as shown below:

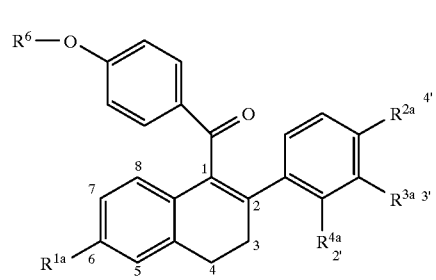

wherein
  $R^{1a}$ is —H or —OR$^7$ in which R$^7$ is a hydroxy protecting group;
  $R^{2a}$, $R^{3a}$, and $R^{4a}$ are, independently, —H, —Cl, —F, $C_1$-$C_4$ alkyl, —OR$^7$ in which R$^7$ is a hydroxy protecting group, with the proviso that $R^{3a}$ and $R^{4a}$ are not both hydrogen; and $R^6$ is —OH or —OCH$_3$.

Further, the present invention provides intermediate compounds of formula VIIIA and VIIIB which are useful for preparing the pharmaceutically active compounds of the present invention, and are shown below:

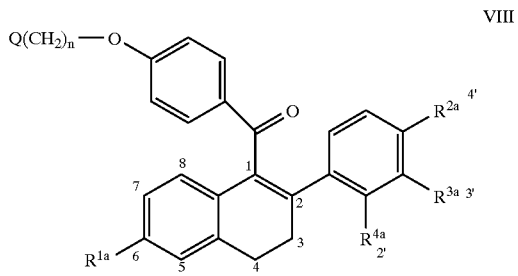

VIII wherein $R^{1a}$ is —H or —OR$^7$ in which R$^7$ is a hydroxy protecting group;

$R^{2a}$, $R^{3a}$, and $R^{4a}$ are, independently, —H, —Cl, —F, C$_1$–C$_4$ alkyl, or —OR$^7$ in which R$^7$ is a hydroxy protecting group, with the proviso that $R^{3a}$ and $R^{4a}$ are not both hydrogen;

n is 2 or 3; and

Q is a leaving group.

The present invention further relates to pharmaceutical compositions containing compounds of formula I.

The present invention still further provides methods for the therapeutic use of such compounds and compositions.

General terms used in the description of compounds herein described bear their usual meanings. For example, "C$_1$–C$_6$ alkyl" refers to straight or branched aliphatic chains of 1 to 6 carbon atoms including moieties such as methyl, ethyl, propyl, isopropyl, butyl, n-butyl, pentyl, isopentyl, hexyl, isohexyl, and the like. Similarly, the term "—OC$_1$–C$_4$ alkyl" represents a C$_1$–C$_4$ alkyl group attached through an oxygen molecule and include moieties such as, for example, methoxy, ethoxy, n-propoxy, isopropoxy, and the like. Of these alkoxy groups, methoxy is highly preferred in most circumstances. Optionally substituted phenyl includes phenyl and phenyl substituted once or twice with C$_1$–C$_6$ alkyl, C$_1$–C$_4$ alkoxy, hydroxy, nitro, chloro, fluoro, or tri (chloro or fluoro)methyl.

The term, "hydroxy protecting group" contemplates numerous functionalities used in the literature to protect a hydroxyl function during a chemical sequence and which can be removed to yield the phenol. Included within this group are acyls, mesylates, tosylates, benzyl, alkylsilyloxys, C$_1$–C$_4$ alkyls, and the like. Numerous reactions for the formation and removal of such protecting groups are described in a number of standard works including, for example, *Protective Groups in Organic Chemistry*, Plenum Press (London and New York, 1973); Green, T. W., *Protective Groups in Organic Synthesis*, Wiley, (New York, 1981); and *The Peptides*, Vol. I, Schrooder and Lubke, Academic Press (London and New York, 1965). Methods for removing preferred R$^7$ hydroxy protecting groups, particularly methyl, are essentially as described in Example 4, infra.

The term, "leaving group" means a chemical entity which is capable of being displaced by an amino function via an SN$_2$ reaction. Such reactions are well known in the art and such groups would include halogens, mesylates, tosylates, and the like. A preferred group is bromo.

The term "inhibit" includes its generally accepted meaning which includes prohibiting, preventing, restraining, and slowing, stopping or reversing progression, severity, or a resultant symptom. As such, the present method includes both medical therapeutic and/or prophylactic administration, as appropriate.

For the following discussion, formula I includes formula Ia and formula Ib.

The starting material for preparing compounds of the present invention is a compound of formula III

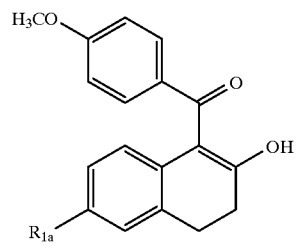

III wherein $R^{1a}$ is —H or —OR$^7$ in which R$^7$ is a hydroxy protecting group. A preferred protecting group is methyl.

Compounds of formula III are well known in the art and are prepared essentially as described by Jones et al., in U.S. Pat. No. 4,400,543 and Jones, et al., in U.S. Pat. No. 5,147,880 the disclosures of which are herein incorporated by reference. See., also, Jones et al., *J. Med. Chem.*, 35:931–8 (1992) and Jones, et al., *J. Med. Chem.*, 22:962 (1979).

In preparing compounds of the present invention, generally, a 1-acylated-2-tetralone of formula III (written in its enolic form) is treated with a base to form its corresponding anion, which is then reacted with diphenylchlorophosphate, providing an enol phosphate derivative of formula IV. The formula IV compound undergoes formal addition-elimination when treated with an aryl Grignard reagent (V), which results in substitution of the 2-phosphate substituent by the aryl moiety, thereby producting a compound of formula IIA'. Dealkylation of formula IIA' compound by a thiolate anion demethylation reagent selectives dealkylates the group which is located para to the electron-withdrawing carbonyl group. The result of such selective dealkylation is a phenolic compound of formula IIA", which serves as an intermediate to the compounds of this invention. This synthetic route is as shown below in Scheme I, where $R^{1a}$, $R^{2a}$, $R^{3a}$, and $R^{4a}$ have their previous meanings and provisions.

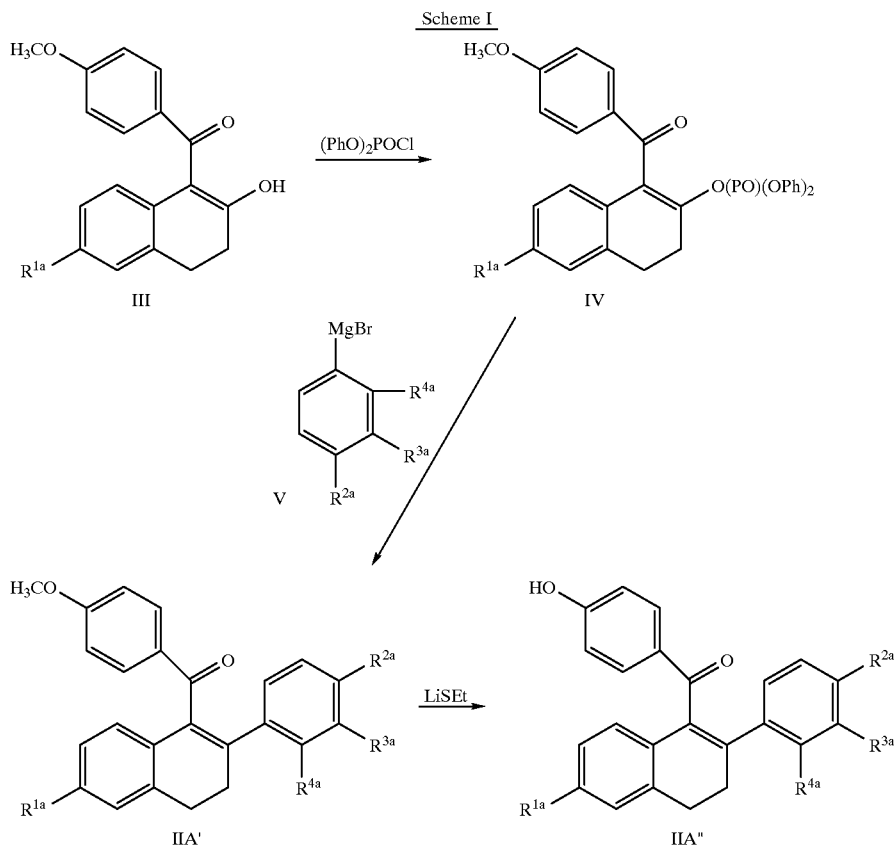

Scheme I

In particular, a formula III enolic compound is phosphorylated by one or more equivalents of a phosphorylating reagent which is a diarylchloro- or diarylbromo-phosphate and preferably diphenylchlorophosphate. This reaction may be carried out in a variety of inert solvents including ethers, THF, dioxane, ethyl acetate, toluene, and acetonitrile, and in the presence of an acid scavenger, such as an alkali metal hydride, alkali metal hydroxide, or alkali metal carbonate or a trialkyl amine such as triethyl amine. The alkali metal base or tertiary amine may also act as a basic catalyst in the phosphorylation process. Although it is preferable to run the reaction at ice bath temperature in order to avoid unwanted side products, elevated temperatures may also be employed, but they are usually unnecessary to complete the phosphorylation reaction. The product of the phosphorylation reaction, an enol phosphate derivative of formula IV, is isolated by usual techniques, such as chromatography. However, it is most convenient to generate the enolphosphate using a solvent/acid scavenger combination which is compatible with the next step of the reaction, the additon of a Grignard reagent. Thus, the combination of sodium hydride in THF under a nitrogen atmosphere is preferred, and leads to a rapid phosphorylation which provides a compound of formula IV.

The intermediate enol phosphate (a compound of formula IV), either isolated or generated in situ, is then reacted with one or more equivalents of an aryl Grignard reagent or an aryl lithium organocuprate reaent. One to two equivalents of an aryl magnesium bromide(V) is preferred. Such Grignard reagents would include, but are not limited to: 3-methoxyphenyl magnesium bromide, 3-chlorophenyl magnesium bromide, 2-methoxyphenyl magnesium bromide, 3-fluorophenyl magnesium bromide, 3-methylphenyl magnesium bromide, 2-methylphenyl magnesium bromide, 2-methyl-3-methoxyphenyl magnesium bromide, 3-methoxy-4-fluorophenyl magnesium bromide, 2-chloro-4-methoxyphenyl magnesium bromide, 3,4-dimethoxyphenyl magnesium bromide, 3-fluoro-4-methoxyphenyl magnesium bromide, and the like. The reaction is typically conducted at ice bath temperature to minimize side reactions, but elevated temperatures may be used to increase the rate of the reaction. The addition of the aryl moiety, followed by the elimination of the phosphate leaving group (formally a 1,4-addition, elimination process) gives rise to a dihydronaphthalene derivative of formula IIA', which is then isolated by conventional techniques such as crystallization or chromatography.

The resulting dihydronaphthalene derivative of formula IIA' is then demethylated to provide an intermediate of formula IIA", which completes the chemical sequence as shown in Scheme I. In order to accomplish regioselective demethylation at the methoxy group para to the carbonyl, a nucleophilic demethylation reagent is used, and alkali metal thiolates (alkali metal salt of an organic thiol) are preferred. Especially preferred are lithium thioethylate or lithium thiomethylate, in excess to the extent of about 1.2 or more equivalents of the demethylation reagent over the substrate. The reaction is conducted under an inert atmosphere to preserve the demethylation reagent and in a solvent which is practically inert to the nucleophilic nature of the thiolate reagent. Suitable solvents for the demethylation are those which are most conducive to bimolecular nucleophilic displacement reactions, and these include dimethylsulfoxide dimethylformamide, dimethylacetamide, and THF. Anhydrous dimethylformamide is a preferred solvent. In order to simultaneously achieve a satisfactory reaction rate and also obtain good control of the selectivity for demethylation at the site para to the carbonyl group, it is important to carefully control the temperature of the reaction. Although the demethylation process will generally take place in the range of temperatures from about 60° C. to 120° C., it is advantageous to use a temperature in the range of about 80°–90° C. to optimize the yield of the desired product. A temperature of about 80° C. is particularly preferred. Under the preferred reaction conditions, the transformation from a formula IIA' compound to a formula IIA" compound is complete after heating for about 2 to 4 hours at the indicated temperature.

Naphthalene compounds of structure IIB are prepared by a dehydrogenation reaction of the corresponding dihydronaphthalene (IIA) compound, followed by an analogous demethylation process as shown in Scheme II below.

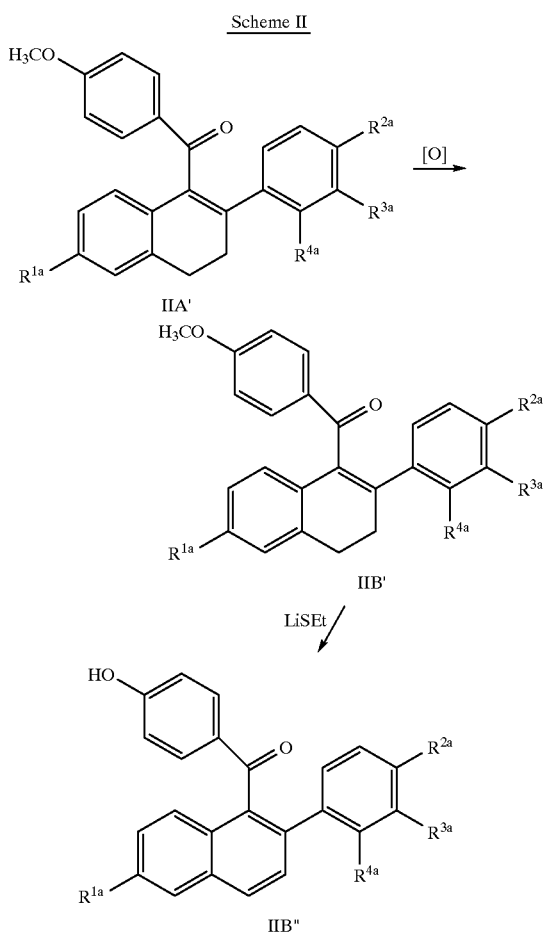

wherein
$R^{ia}$, $R^{2a}$, $R^{3a}$, and $R^{4a}$ have their previous meanings and provisions.

Appropriate oxidants for the first reaction step shown in Scheme II are limited to those known in the art which can cause the loss of hydrogen from a saturated system to give an aromatized system. Such oxidants include, for example, dehydrogen catalysts such as platinum, palladium, and nickel, elemental sulfur and selenium, and quinones. For the present application, quinone oxidants, especially 2,3-dichloro-5,6-dicyano-1,4-benzoquinone (DDQ) are preferred. About 1 to 2 equivalents of DDQ per equivalent of substrate will drive the present process phase. The reaction is conducted in an inert solvent, preferably 1,4-dioxane, and at elevated temperature, preferably at reflux. Under the preferred conditions, the reaction is complete in about 1 to 24 hours.

Compound IIB' is converted to the hydroxy compound IIB" using the same demethylation procedure described, supra.

Compounds of formula IIA', IIA", IIB', and IIB" collectively are novel intermediate compounds of formula II which are useful for the preparation of pharmaceutically active compounds of formula I of the present invention. Compounds of formula II would include, but are not limited to:

[2-(3-methoxyphenyl)-3,4-dihydro-6-methoxynaphthalen-1-yl][4-methoxyphenyl]methanone

[2-(3-methoxyphenyl)-3,4-dihydro-6-methoxynaphthalen-1-yl][4-hydroxyphenyl]methanone

[2-(3-methoxyphenyl)-3,4-dihydro-naphthalen-1-yl][4-methoxyphenyl]methanone

[2-(3-methoxy-4-methylphenyl)-3,4-dihydro-naphthalen-1-yl][4-hydroxyphenyl]methanone

[2-(2-methoxyphenyl)-3,4-dihydro-6-methoxynaphthalen-1-yl][4-methoxyphenyl]methanone

[2-(3,4-di-methoxyphenyl)-3,4-dihydro-6-methoxynaphthalen-1-yl][4-methoxyphenyl]methanone

[2-(3,4-di-methoxyphenyl)-3,4-dihydro-6-methoxynaphthalen-1-yl][4-hydroxyphenyl]methanone

[2-(3-chlorophenyl)-3,4-dihydro-6-methoxynaphthalen-1-yl][4-methoxyphenyl]methanone

[2-(2-methoxy-3-fluorophenyl)-3,4-dihydro-6-methoxynaphthalen-1-yl][4-methoxyphenyl]methanone

[2-(2-methyl-2-methyl-3-methoxyphenyl)-3,4-dihydro-6-methoxynaphthalen-1-yl][4-hydroxyphenyl]methanone

[2-(3-methoxy-4-fluorophenyl)-3,4-dihydro-naphthalen-1-yl][4-methoxyphenyl]methanone

[2-(2-chloro-3-methoxyphenyl)-3,4-dihydro-6-methoxynaphthalen-1-yl][4-hydroxyphenyl]methanone

[2-(2-ethyl-4-methoxyphenyl)-3,4-dihydro-6-methoxynaphthalen-1-yl][4-hydroxyphenyl]methanone

[2-(2,4-dimethyl-3-methoxyphenyl)-3,4-dihydro-naphthalen-1-yl][4-methoxyphenyl]methanone

[2-(2-chloro-3-methoxy-4-fluorophenyl)-3,4-dihydro-6-methoxynaphthalen-1-yl][4-hydroxyphenyl]methanone

[2-(3-methoxyphenyl)-6-methoxynaphthalen-1-yl][4-methoxyphenyl]methanone

[2-(3-methoxyphenyl)-6-hydroxynaphthalen-1-yl][4-methoxyphenyl]methanone

[2-(2-methoxyphenyl)-6-methoxynaphthalen-1-yl][4-methoxyphenyl]methanone

[2-(2-methoxyphenyl)-6-hydroxynaphthalen-1-yl][4-methoxyphenyl]methanone

[2-(2,3-di-methoxyphenyl)-6-methoxynaphthalen-1-yl][4-methoxyphenyl]methanone

[2-(3-methoxyphenyl)-naphthalen-1-yl][4-methoxyphenyl]methanone

[2-(3-methoxyphenyl)-naphthalen-1-yl][4-hydroxyphenyl]methanone

[2-(2,4-di-methoxyphenyl)-6-methoxynaphthalen-1-yl][4-methoxyphenyl]methanone

[2-(3-methylphenyl)-6-methoxynaphthalen-1-yl][4-methoxyphenyl]methanone

[2-(2-ethyl-3-chlorophenyl)-6-methoxynaphthalen-1-yl][4-methoxyphenyl]methanone

[2-(3-fluorophenyl)-6-methoxynaphthalen-1-yl][4-methoxyphenyl]methanone

[2-(3-methox4-fluorophenyl)-6-methoxynaphthalen-1-yl][4-methoxyphenyl]methanone
[2-(3-methoxy-4-fluorophenyl)-6-methoxynaphthalen-1-yl][4-hydroxyphenyl]methanone
[2-(2,4-di-methoxyphenyl)-naphthalen-1-yl][4-hydroxyphenyl]methanone
[2-(2-fluoro-3-methoxyphenyl)-6-methoxynaphthalen-1-yl][4-methoxyphenyl]methanone
[2-(2-chloro-3-methoxy-4-fluorophenyl)-6-methoxynaphthalen-1-yl][4-methoxyphenyl]methanone Upon preparation of a formula IIA" or IIB" compound, it is then reacted with a compound of formula VI $$R^5-(CH_2)_n-Q \qquad VI$$

wherein $R^5$ and n are as defined above, and Q is a bromo or, preferably, a chloro moiety, or a salt thereof, to form a compound of formula IA' or IB'. The formula IA' or IB' compound is then deprotected, when $R^7$ hydroxy protecting groups are present, to form a compound of formula IA" or IB". These process steps are shown in Scheme III below.

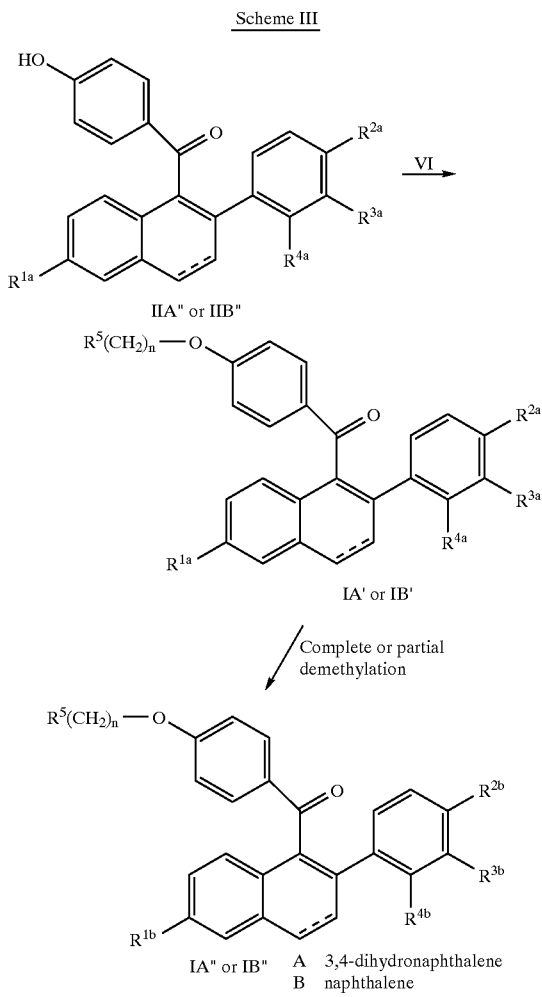

wherein:
$R^{1a-4a}$, n, and $R^5$ have their previous meanings and provisions.
$R^{1b}$ is —H, —OH, or —OCH$_3$;
$R^{2b}$, $R^{3b}$, and $R^{4b}$ are, independently, —H, —Cl, —F, —OH, —OCH$_3$, or C$_1$–C$_4$ alkyl, with the proviso that $R^{3b}$ and $R^{4b}$ are not both hydrogen;

or a pharmaceutically acceptable salt or solvate thereof.

In the first step of the process shown in Scheme III, the alkylation is carried out via standard procedures. Compounds of formula VI are commercially available or are prepared by means well known to one of ordinary skill in the art. Compounds of formula VI would include, but are not limited to:
1-(2-chloroethyl)piperidine hydrochloride, 1-(2-chloroethyl)pyrrolidine hydrochloride, 1-(2-chloroethyl) hexamethyleneimino hydrochloride, 1-(3-chloropropyl) piperidine hydrochloride, 1-(3-chloropropyl)-2-methylpyrrolidine hydrochloride, 2-chloroethyl-N,N-dimethylamine hydrochloride, 3-chloro-N,N-diethylamine hydrochloride,1-(2-chloroethyl)piperidine, 1-(2-chloroethyl)-3,3-dimethylpyrrolidine hydrochloride, 1-(2-chloroethyl)-3-methylpyrrolidine hydrochloride, 1-(3-chloropropyl)piperidine hydrochloride, 1-(3-chloropropyl)hexamethyleneimino hydrochloride, and the like. Preferably, the hydrochloride salt of a formula V compound, particularly 2-chloroethylpiperidine hydrochloride, is used.

Generally, one equivalent of formula IIA" or IIB" substrate is reacted with 2 equivalents of a formula VI compound in the presence of at least about 4 equivalents of an alkali metal carbonate, preferably cesium carbonate or potassium carbonate, and an appropriate solvent.

Solvents for this reaction are those solvents or mixture of solvents which remain inert throughout the reaction. N,N-dimethylformamide, especially the anhydrous form thereof, is preferred.

The temperature employed in this step should be sufficient to effect completion of this alkylation reaction. Often ambient temperature is sufficient and preferred, but in certain cases, higher temperatures may be required.

The present reaction preferably is run under an inert atmosphere, particularly nitrogen.

Under the preferred reaction conditions, this reaction will run to completion in about 16 to about 20 hours. Of course, the progress of the reaction can be monitored via standard chromatographic techniques.

As an alternative for preparing compounds of formulae IA', IA", IB', or IB", a formula IIA" or IIB" compound is reacted with an excess of a bis-alkylating agent of the formula $$Q-(CH_2)n-Q'$$

wherein Q and Q' each are the same or different leaving group and n is two or three, in an alkali solution. This sequence is illustrated in the first reaction in Scheme IV, below. Appropriate leaving groups include the sulfonates such as methanesulfonate, 4-bromobenzenesulfonate, toluenesulfonate, ethanesulfonate, isopropylsulfonate, 4-methoxybenzenesulfonate, 4-nitrobenzenesulfonate, 2-chlorobenzenesulfonate, triflate, and the like, halogens such as bromo, chloro, and iodo, and other related leaving groups. Halogens are preferred leaving groups and bromo is especially preferred.

A preferred alkali solution for this alkylation reaction contains potassium carbonate in an inert solvent such as, for example, methylethyl ketone (MEK) or DMF. In this solution, the 4-hydroxy group of the benzoyl moiety of a formula III compound exists as a phenoxide ion which displaces one of the leaving groups of the alkylating agent.

This reaction is best when the alkali solution containing the reactants and reagents is brought to reflux and allowed to run to completion. When using MEK as the preferred solvent, reaction times run from about 6 hours to about 20 hours.

Scheme IV

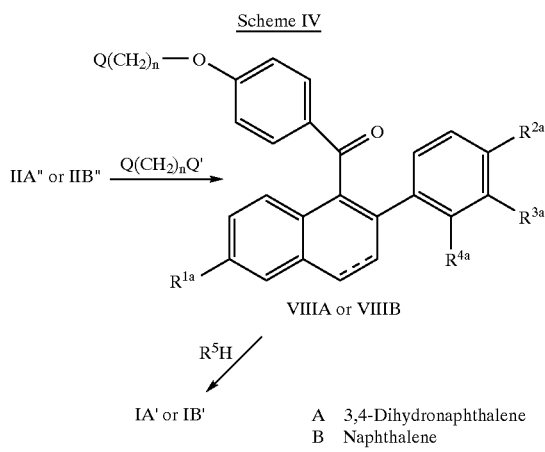

A   3,4-Dihydronaphthalene
B   Naphthalene wherein: $R^{1a}$, $R^{2a}$, $R^{3a}$, $R^{4a}$, $R^5$, n, and Q have their previous meanings and provisions.

Application of the chemistry outlined, supra., provides for the synthesis of the novel and useful compounds of formula VIII. These compounds would include, but are not limited to:

[2-(2-fluoro-3-methoxyphenyl)-6-methoxynaphthalen-1-yl] [4-(2-bromoethoxy)phenyl]methanone

[2-(3-methoxyphenyl)-6-methoxynaphthalen-1-yl][4-(2-bromoethoxy)phenyl]methanone

[2-(3-methoxyphenyl)naphthalen-1-yl][4-(2-bromoethoxy) phenyl]methanone

[2-(3-methoxyphenyl)-6-methoxynaphthalen-1-yl][4-(3-bromopropoxy)phenyl]methanone   [2-(2-methoxyphenyl)-6-methoxynaphthalen-1-yl][4-(2-bromoethoxy)phenyl]methanone

[2-(3-fluoro-4-methoxyphenyl)-6-methoxynaphthalen-1-yl] [4-(2-bromoethoxy)phenyl]methanone

[2-(3-methoxy-4-chlorophenyl)-6-methoxynaphthalene-1-yl][4-(2-bromoethoxy)phenyl]methanone

[2-(3-methoxyphenyl)-6-methoxy-3,4-dihydronaphthalene-1-yl][4-(2-bromoethoxy)phenyl]methanone

[2-(2-methoxyphenyl)-6-methoxy-3,4-dihydronaphthalene-1-yl][4-(2-bromoethoxy)phenyl]methanone

[2-(3-methoxyphenyl)-6-methoxy-3,4-dihydronaphthalene-1-yl][4-(3-bromopropoxy)phenyl]methanone

[2-(3-methoxy-4-fluorophenyl)-6-methoxy-3,4-dihydronaphthalen-1-yl][4-(2-bromoethoxy)phenyl]methanone

[2-(3-chlorophenyl)-6-methoxy-3,4-dihydronaphthalene-1-yl][4-(2-bromoethoxy)phenyl]methanone

[2-(3-methyl-4-methoxyphenyl)-3,4-dihydronaphthalene-1-yl][4-(2-bromoethoxy)phenyl]methanone

[2-(2-chloro-3-methoxyphenyl)-6-methoxy-3,4-dihydronaphthalene-1-yl][4-(2-bromoethoxy)phenyl] methanone and the like.

The reaction product from this step (VIIIA or VIIIB) is then reacted with 1-piperidine, 1-pyrrolidine, methyl-1-pyrrolidine, dimethyl-1-pyrrolidine, 4-morpholine, dimethylamine, diethylamine, or 1-hexamethyleneimine, or other secondary amines, via standard techniques, to form compounds of formula IA' or IB', as seen the second reaction in Scheme IV, supra. Preferably, the hydrochloride salt of piperidine is reacted with the alkylated compound of formula VIIIA or VIIIB in an inert solvent, such as anhydrous DMF, and heated to a temperature in the range from about 60° C. to about 110° C. When the mixture is heated to a preferred temperature of about 90° C., the reaction only takes about 30 minutes to about 1 hour. However, changes in the reaction conditions will influence the amount of time this reaction needs to be run to completion. Of course, the progress of this reaction step may be monitored via standard chromatographic techniques.

An alternative route for preparing compounds IA of the present invention is depicted in Scheme V, below, in which: $R^{1a}$, $R^{2a}$, $R^{3a}$, $R^{4a}$, $R^5$, and n have their previous meanings and provisions.

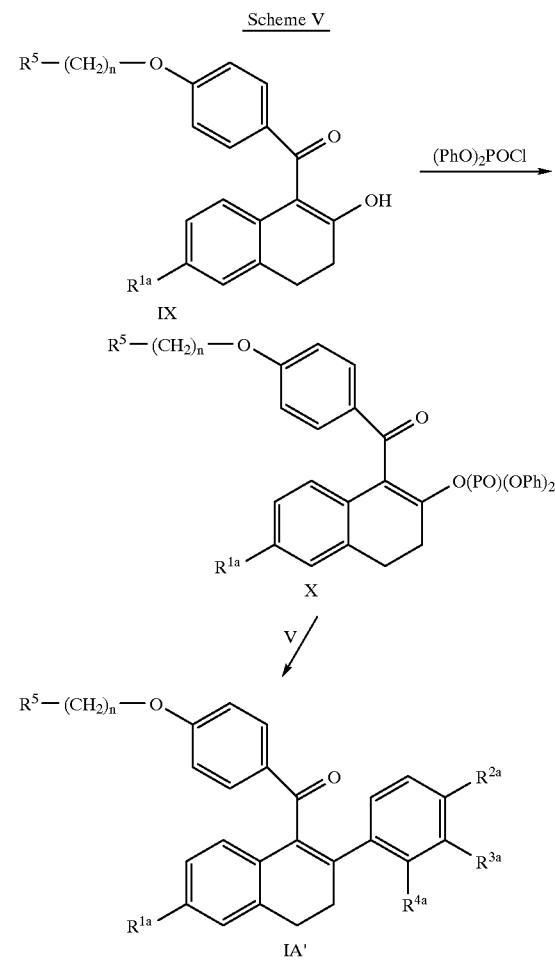

Scheme V

In this alternative, the starting material is a 1-acylated-2-tetralone of formula IX which already includes the basic side chain moiety. The compound of formula IX is treated with a base to form its corresponding anion, which is reacted with diphenylchlorophosphate, providing an enol phosphate derivative of formula X. The formula X compound undergoes formal addition-elimination when treated with an aryl Grignard reagent (V), which results in substitution of the 2-phosphate substituent by the aryl moiety, thereby producing directly a formula IA' compound of this invention.

The compounds of formula IX are prepared by the methods described in the references, supra. The further reactions outlined in Scheme V are analogous to those described for Scheme I.

Compounds of formula IA' and IB' in which $R^7$, when present, is $C_1$–$C_4$ alkyl, preferably methyl, are pharmaceutically active for the methods herein described. Accordingly, such compounds are encompassed by the definition herein of compounds of formula I. Compounds of formula IA' and IB' would include, but are not limited to

[2-(3-methoxyphenyl)-6-methoxynaphthalen-1-yl][4-[2-(1-piperidinyl)ethoxy]phenyl]methanone

[2-(3-methoxyphenyl)naphthalen-1-yl][4-[2-(1-piperidinyl)ethoxy]phenyl]methanone

[2-(2-methoxyphenyl)-6-methoxynaphthalen-1-yl][4-[2-(1-piperidinyl)ethoxy]phenyl]methanone

[2-(3-methoxyphenyl)-6-methoxynaphthalen-1-yl][4-[2-(1-pyrolidinyl)ethoxy]phenyl]methanone

[2-(3-methoxyphenyl)-6-methoxynaphthalen-1-yl][4-[3-(1-piperidinyl)propoxy]phenyl]methanone

[2-(3-methoxy-4-fluorophenyl)-6-methoxynaphthalen-1-yl][4-[2-(1-piperidinyl)ethoxy]phenyl]methanone

[2-(2-methyl-3-methoxyphenyl)-6-methoxynaphthalen-1-yl][4-[2-(1-piperidinyl)ethoxy]phenyl]methanone

[2-(3-chloro-4-methoxyphenyl)-6-methoxynaphthalen-1-yl][4-[2-(1-piperidinyl)ethoxy]phenyl]methanone

[2-(3-methoxyphenyl)-6-methoxynaphthalen-1-yl][4-[2-(1-hexamethylenimino)ethoxy]phenyl]methanone

[2-(3,4-di-methoxyphenyl)-6-methoxynaphthalen-1-yl][4-[2-(1-piperidinyl]ethoxylphenyl]methanone

[2-(2,3-di-methoxyphenyl)-6-methoxynaphthalen-1-yl][4-[2-(1-piperidinyl)ethoxy]phenyl]methanone

[2-(3-methyl-4-methoxyphenyl)-6-methoxynaphthalen-1-yl][4-[3-(1-piperidinyl)propoxy]phenyl]methanone

[2-(2-fluoro-3-methoxyphenyl)naphthalen-1-yl][4-[2-(1-piperidinyl)ethoxy]phenyl]methanone

[2-(2-ethyl-3-methoxyphenyl)-6-methoxynaphthalen-1-yl][4-[2-(1-(2-methylpyrolidinyl)ethoxy]phenyl]methanone

[2-(3-methoxyphenyl)-6-methoxynaphthalen-1-yl][4-[2-(1-(3,3-dimethylpyrolidinyl)ethoxy]phenyl]methanone

[2-(2-methoxy-4-chlorophenyl)-6-methoxynaphthalen-1-yl][4-[2-(1-piperidinyl)ethoxy]phenyl]methanone

[2-(3-methoxyphenyl)-3,4-dihydro-6-methoxynaphthalen-1-yl][4-[2-(1-piperidinyl)ethoxy]phenyl]methanone

[2-(3-methoxyphenyl)-3,4-dihydronaphthalen-1-yl][4-[2-(1-piperidinyl)ethoxy]phenyl]methanone

[2-(2-methoxyphenyl)-3,4-dihydro-6-methoxynaphthalen-1-yl][4-[2-(1-piperidinyl)ethoxy]phenyl]methanone

[2-(3-methoxyphenyl)3,4-dihydro-6-methoxynaphthalen-1-yl][4-[2-(1-pyrolidinyl)ethoxy]phenyl]methanone

[2-(3-methoxyphenyl)3,4-dihydro-6-methoxynaphthalen-1-yl][4-[3-(1-piperidinyl)propoxy]phenyl]methanone

[2-(3-methoxy-4-fluorophenyl)-3,4-dihydro-6-methoxynaphthalen-1-yl][4-[2-(1-piperidinyl)ethoxy]phenyl]methanone

[2-(2-methyl-3-methoxyphenyl)-3,4-dihydro-6-methoxynaphthalen-1-yl][4-[2-(1-piperidinyl)ethoxy]phenyl]methanone

[2-(3-chloro-4-methoxyphenyl)-3,4-dihydro-6-methoxynaphthalen-1-yl][4-[2-(1-piperidinyl)ethoxy]phenyl]methanone

[2-(3-methoxyphenyl)-3,4-dihydro-6-methoxynaphthalen-1-yl][4-[2-(1-hexamethylenimino)ethoxy]phenyl]methanone

[2-(3,4-di-methoxyphenyl)-3,4-dihydro-6-methoxynaphthalen-1-yl][4-[2-(1-piperidinyl)ethoxy]phenyl]methanone Other preferred compounds of formula I are obtained by cleaving, when present, the $R^7$ hydroxy protecting group of formula IA' and IB' compounds via well known procedures. Such procedures are cited in the references, supra. There is one exception to these general methods and involves those compounds of formula IA' and IB', wherein $R^{3a}$ is an oxygen-containing group. In the case of these compounds, standard demethylating procedures, such as, the use of Lewis acids, e.g., $BCl_3$, $AlCl_3$, $PBr_3$, and the like, leads to the formation of undesired by-products and the desired compounds (IA" or IB") can not be obtained. However, these compounds, where $R^3$ is hydroxy may be obtained by cleavage of the methoxy protecting group under basic conditions, such as LiSEt. Compounds of formula IA" and IB" are pharmaceutically active for the methods herein described, and thus they are encompassed by formula I as defined herein.

Compounds of formula IA" and IB" would include, but not be limited to:

[2-(3-hydroxyphenyl)-6-hydroxynaphthalen-1-yl][4-[2-(1-piperidinyl)ethoxy]phenyl]methanone

[2-(3-hydroxyphenyl)-6-methoxynaphthalen-1-yl][4-[2-(1-piperidinyl)ethoxy]phenyl]methanone

[2-(3-methoxyphenyl)-6-hydroxynaphthalen-1-yl][4-[2-(1-piperidinyl)ethoxy]phenyl]methanone

[2-(3-hydroxyphenyl)naphthalen-1-yl][4-[2-(1-piperidinyl)ethoxy]phenyl]methanone

[2-(3-hydroxyphenyl)-6-hydroxynaphthalen-1-yl][4-[2-(1-pyrolidinyl)ethoxy]phenyl]methanone

[2-(3-hydroxyphenyl)-6-hydroxynaphthalen-1-yl][4-[3-(1-piperidinyl)propoxy]phenyl]methanone

[2-(3-hydroxy-4-fluorophenyl)-6-hydroxynaphthalen-1-yl][4-[2-(1-piperidinyl)ethoxy]phenyl]methanone

[2-(2-hydroxyphenyl)-6-hydroxynaphthalen-1-yl][4-[2-(1-piperidinyl)ethoxy]phenyl]methanone

[2-(3-hydroxyphenyl)-6-hydroxynaphthalen-1-yl][4-[2-(1-hexamethyleneimino)ethoxy]phenyl]methanone

[2-(2-methyl-3-hydroxyphenyl)-6-hydroxynaphthalen-1-yl][4-[2-(1-piperidinyl)ethoxy]phenyl]methanone

[2-(3,4-di-hydroxyphenyl)-6-hydroxynaphthalen-1-yl][4-[2-(1-piperidinyl)ethoxy]phenyl]methanone

[2-(3-hydroxyphenyl)-3,4-dihydro-6-hydroxynaphthalen-1-yl][4-[2-(1-piperidinyl)ethoxy]phenyl]methanone

[2-(3-hydroxyphenyl)-3,4-dihydro-naphthalen-1-yl][4-[2-(1-piperidinyl)ethoxy]phenyl]methanone

[2-(3-methoxyphenyl)-3,4-dihydro-6-hydroxynaphthalen-1-yl][4-[2-(1-piperidinyl)ethoxy]phenyl]methanone

[2-(3-hydroxyphenyl)-3,4-dihydro-6-methoxynaphthalen-1-yl][4-[2-(1-piperidinyl)ethoxy]phenyl]methanone

[2-(3-hydroxyphenyl)-3,4-dihydro-6-hydroxynaphthalen-1-yl][4-[2-(1-pyrolidinyl)ethoxy]phenyl]methanone

[2-(3-hydroxyphenyl)-3,4-dihydro-6-hydroxynaphthalen-1-yl][4-[3-(1-piperidinyl)propoxy]phenyl]methanone

[2-(2-hydroxyphenyl)-3,4-dihydro-6-hydroxynaphthalen-1-yl][4-[2-(1-piperidinyl)ethoxy]phenyl]methanone

[2-(3,4-di-hydroxyphenyl)-3,4-dihydro-6-hydroxynaphthalen-1-yl][4-[2-(1-piperidinyl)ethoxy]phenyl]methanone

[2-(3-hydroxy-4-chlorophenyl)-3,4-dihydro-6-hydroxynaphthalen-1-yl][4-[2-(1-piperidinyl)ethoxy]phenyl]methanone

[2-(2-fluoro-3-hydroxyphenyl)-3,4-dihydronaphthalen-1-yl][4-[2-(1-piperidinyl)ethoxy]phenyl]methanone Other preferred compounds of formula I are prepared by replacing the 6- and/or 2', 3', or 4'-position hydroxy moieties, when present, with a moiety of the formula —O—CO—($C_1$–$C_6$ alkyl), or —O—$SO_2$—($C_2$–$C_6$ alkyl) via well known procedures (See, for example, U.S. Pat. Nos. 5,393,763 and 5,482,949, each of which is herein incorporated by reference.)

For example, when an —O—CO($C_1$–$C_6$ alkyl) group is desired, a mono- or dihydroxy compound of formula IA" or IB" is reacted with an acylating agent such as acyl chloride, bromide, cyanide, or azide, or with an appropriate anhydride or mixed anhydride. The reactions are conveniently carried out in a basic solvent such as pyridine, lutidine, quinoline or isoquinoline, or in a tertiary amine solvent such as triethylamine, tributylamine, methylpiperidine, and the like. The reaction also may be carried out in an inert solvent such as ethyl acetate, dimethylformamide, dimethylsulfoxide, dioxane, dimethoxyethane, acetonitrile, acetone, methyl ethyl ketone, and the like, to which at least one equivalent of an acid scavenger (except as noted below), such as a tertiary amine, has been added. If desired, acylation catalysts such as 4-dimethylaminopyridine or 4-pyrrolidinopyridine may be used. See, for example, Haslam, et al., *Tetrahedron*, 36:2409–2433 (1980).

The present reactions are carried out at moderate temperatures, in the range from about −25° C. to about 100° C., frequently under an inert atmosphere such as nitrogen gas. However, ambient temperature is usually adequate for the reaction to run.

Acylation of a 6-position and/or 2', 3', or 4'-position hydroxy group also may be performed by acid-catalyzed reactions of the appropriate carboxylic acids in inert organic solvents. Acid catalysts such as sulfuric acid, polyphosphoric acid, methanesulfonic acid, and the like are used.

The aforementioned $R^1$, $R^2$, $R^3$, and $R^4$ groups of formula I compounds also may be provided by forming an active ester of the appropriate acid, such as the esters formed by such known reagents such as dicyclohexylcarbodiimide, acylimidazoles, nitrophenols, pentachlorophenol, N-hydroxysuccinimide, and 1-hydroxybenzotriazole. See, for example, *Bull. Chem. Soc. Japan*, 38:1979 (1965), and *Chem. Ber.*, 788 and 2024 (1970).

Each of the above techniques which provide —O—CO—($C_1$–$C_6$ alkyl) moieties are carried out in solvents as discussed above. Those techniques which do not produce an acid product in the course of the reaction do not require the use of an acid scavenger in the reaction mixture.

When a formula I compound is desired in which the 6- and/or 2', 3' or 4'-position hydroxy group of a formula IA" or IB" compound is converted to a group of the formula —O—$SO_2$—($C_2$–$C_6$ alkyl), the mono- or dihydroxy compound is reacted with, for example, a sulfonic anhydride or a derivative of the appropriate sulfonic acid such as a sulfonyl chloride, bromide, or sulfonyl ammonium salt, as taught by King and Monoir, *J. Am. Chem. Soc.*, 97:2566–2567 (1975). The dihydroxy compound may also be reacted with the appropriate sulfonic anhydride or mixed sulfonic anhydrides. Such reactions are carried out under conditions such as were explained above in the discussion of reaction with acid halides and the like.

Thus, the chemical pathways outlined, supra, provide for the compounds of the current invention, i.e., the compounds of formula I, including IA and IB. The compounds of formula I would include, but are not limited to:

[2-(3-acetyloxyphenyl)-6-acetyloxynaphthalen-1-yl][4-[2-(1-piperidinyl)ethoxy]phenyl]methanone
[2-(3-acetyloxyphenyl)-6-methoxynaphthalen-1-yl][4-[2-(1-piperidinyl)ethoxy]phenyl]methanone
[2-(3-methoxyphenyl)-6-acetyloxynaphthalen-1-yl][4-[2-(1-piperidinyl)ethoxy]phenyl]methanone
[2-(3-butyroyloxyphenyl)naphthalen-1-yl][4-[2-(1-piperidinyl)ethoxy]phenyl]methanone
[2-(3-benzoyloxyphenyl)-6-benzoyloxynaphthalen-1-yl][4-[2-(1-piperidinyl)ethoxy]phenyl]methanone
[2-(3-n-butylsulfonoyloxyphenyl)-6-n-butylsulfonoyloxynaphthalen-1-yl][4-[2-(1-piperidinyl)ethoxy]phenyl]methanone
[2-(3-(4-methylbenzoyl)oxyphenyl)naphthalen-1-yl][4-[2-(1-pyrolidinyl)ethoxy]phenyl]methanone
[2-(3-acetyloxyphenyl)-6-acetyloxynaphthalen-1-yl][4-[3-(1-piperidinyl)propoxy]phenyl]methanone
[2-(3-benzoyloxy-4-fluorophenyl)-6-hydroxynaphthalen-1-yl][4-[2-(1-piperidinyl)ethoxy]phenyl]methanone
[2-(2-n-butylsulfonoyloxyphenyl)-6-n-butylsulfonoyloxynaphthalen-1-yl][4-[2-(1-piperidinyl)ethoxy]phenyl]methanone
[2-(3-pentanoyloxyphenyl)-6-pentanoyloxynaphthalen-1-yl][4-[2-(1-hexamethyleneimino)ethoxy]phenyl]methanone
[2-(2-methyl-3-hydroxyphenyl)-6-hexanoyloxynaphthalen-1-yl][4-[2-(1-piperidinyl)ethoxy]phenyl]methanone
[2-(3,4-di-acetyloxyphenyl)-6-acetyloxynaphthalen-1-yl][4-[2-(1-piperidinyl)ethoxy]phenyl]methanone
[2-(3-acetyloxyphenyl)-3,4-dihydro-6-acetyloxynaphthalen-1-yl][4-[2-(1-piperidinyl)ethoxy]phenyl]methanone
[2-(3-benzoyloxyphenyl)-3,4-dihydro-6-benzoyloxynaphthalen-1-yl][4-[2-(1-piperidinyl)ethoxy]phenyl]methanone
[2-(3-acetyloxyphenyl)-3,4-dihydronaphthalen-1-yl][4-[2-(1-piperidinyl)ethoxy]phenyl]methanone
[2-(3-n-butylsulfonoyloxyphenyl)-3,4-dihydro-6-n-butylsulfonoyloxynaphthalen-1-yl][4-[2-(1-piperidinyl)ethoxy]phenyl]methanone
[2-(3-benzoyloxyphenyl)-3,4-dihydro-naphthalen-1-yl][4-[2-(1-piperidinyl)ethoxy]phenyl]methanone
[2-(3-methoxyphenyl)-3,4-dihydro-6-propanoyloxynaphthalen-1-yl][4-[2-(1-piperidinyl)ethoxy]phenyl]methanone
[2-(3-acetyloxyphenyl)-3,4-dihydro-6-methoxynaphthalen-1-yl][4-[2-(1-piperidinyl)ethoxy]phenyl]methanone
[2-(3-pentanoyloxyphenyl)-3,4-dihydro-6-pentanoyloxynaphthalen-1-yl][4-[2-(1-pyrolidinyl)ethoxy]phenyl]methanone
[2-(3-(4-methylbenzoyl)oxyphenyl)-3,4-dihydro-6-(4-methylbenzoyl)oxynaphthalen-1-yl][4-[3-(1-piperidinyl)propoxy]phenyl]methanone
[2-(2-acetyloxyphenyl)-3,4-dihydro-6-benzoyloxynaphthalen-1-yl][4-[2-(1-piperidinyl)ethoxy]phenyl]methanone
[2-(3,4-di-benzoylxyphenyl)-3,4-dihydro-6-methoxynaphthalen-1-yl][4-[2-(1-piperidinyl)ethoxy]phenyl]methanone
[2-(3-acetyloxy-4-chlorophenyl)-3,4-dihydro-6-acetyloxynaphthalen-1-yl][4-[2-(1-piperidinyl)ethoxy]phenyl]methanone
[2-(2-fluoro-3-benzoyloxyphenyl)-3,4-dihydronaphthalen-1-yl][4-[2-(1-piperidinyl)ethoxy]phenyl]methanone Although the free-base form of formula I compounds may be used in the methods of the present invention, it is preferred to prepare and use a pharmaceutically acceptable salt form. Thus, the compounds used in the methods of this invention primarily form pharmaceutically acceptable acid addition salts with a wide variety of organic and inorganic acids, and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. Preferred salts are the hydrochloride and oxalate salts.

The pharmaceutically acceptable acid addition salts are typically formed by reacting a compound of formula I with an equimolar or excess amount of acid. The reactants are generally combined in a mutual solvent such as diethyl ether or ethyl acetate. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

The term "solvate" represents an aggregate that comprises one or more molecules of the solute, such as a formula I compound, with one or more molecules of solvent.

As used herein, the term "effective amount" means an amount of compound of the present invention which is capable of inhibiting, alleviating, ameliorating, treating, or preventing further symptoms in mammals, including humans, suffering from estrogen deprivation, for example, menopause or ovariectomy, or inappropriate estrogen stimulation such as uterine fibrosis or endometriosis, or suffering from aortal smooth muscle cell profileration or restenosis. In the case of estrogen-dependent cancers, the term "effective amount" means the amount of compound of the present invention which is capable of alleviating, ameliorating, inhibiting cancer growth, treating, or preventing the cancer and/or its symptoms in mammals, including humans.

By "pharmaceutically acceptable formulation" it is meant that the carrier, diluent, excipients and salt must be compatible with the active ingredient (a compound of formula I) of the formulation, and not be deleterious to the recipient thereof. Pharmaceutical formulations can be prepared by procedures known in the art. For example, the compounds of this invention can be formulated with common excipients, diluents, or carriers, and formed into tablets, capsules, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agar agar, calcium carbonate, and sodium bicarbonate; agents for retarding dissollution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate and solid polyethylene glycols. Final pharmaceutical forms may be: pills, tablets, powders, lozenges, syrups, aerosols, saches, cachets, elixirs, suspensions, emulsions, ointments, suppositories, sterile injectable solutions, or sterile packaged powders, and the like, depending on the type of excipient used.

Additionally, the compounds of this invention are well suited to formulation as sustained release dosage forms. The formulations can also be so constituted that they release the active ingredient only or preferably in a particular part of the intestinal tract, possibly over a period of time. Such formulations would involve coatings, envelopes, or protective matrices which may be made from polymeric substances or waxes.

The particular dosage of a compound of formula I required to treat, inhibit, or prevent the symptoms and/or disease of a mammal, including humans, suffering from the above maladies according to this invention will depend upon the particular disease, symptoms, and severity. Dosage, routes of administration, and frequency of dosing is best decided by the attending physician. Generally, accepted and effective doses will be from 15 mg to 1000 mg, and more typically from 15 mg to 80 mg. Such dosages will be administered to a patient in need of treatment from one to three times each day or as often as needed for efficacy, normally for at least six months.

The present invention also provides methods for inhibiting estrogen deficient pathologies including, for example, lack of birth control, postmenopausal syndrome including, for example, osteoporosis, cardiovascular disease, restenosis, and hyperlipidemia, certain cancers in men such as protate cancer, acne, hirsutism, dysfunctional uterine bleeding, dysmenorrhea, and atrophic vaginitis comprising administering to a mammal in need of treatment an effective amount of a compound of formula I, and, optionally, an effective amount of a progestin. One of skill in the art will recognize that estrogenic agents have a multitude of applications for treating estrogen deficient pathologies well beyond those listed infra. The present invention contemplates and encompasses such maladies although not specified by name.

Compounds of the current invention may also be used in conjunction with other mixed estrogen agonists/antagonists, especially those which demonstrate increased detrimental stimulation of uterine tissue, such as, for example, tamoxifen, droloxifene, nafoxidene, or clomiphene.

As a further embodiment of the invention, the compounds of formula I may be administered along with an effective amount of an additional therapeutic agent, including but not limited to estrogen, progestin, other benzothiophene compounds including raloxifene, bisphosphonate compounds such as alendronate and tiludronate, parathyroid hormone (PTH), including truncated and/or recombinant forms of PTH such as, for example, PTH (1–34), calcitonin, bone morphogenic proteins (BMPs), or combinations thereof. The different forms of these additional therapeutic agents available as well as the various utilities associated with same and the applicable dosing regimens are well known to those of skill in the art.

Various forms of estrogen and progestin are commercially available. As used herein, the term "estrogen" includes compounds having estrogen activity and estrogen-based agents. Estrogen compounds useful in the practice of the present invention include, for example, estradiol estrone, estriol, equilin, equilenin, estradiol cypionate, estradiol valerate, ethynyl estradiol, polyestradiol phosphate, estropipate, diethylstibestrol, dienestrol, chlorotrianisene, and mixtures thereof. Estrogen-based agents, include, for example, 17-a-ethynyl estradiol (0.01–0.03 mg/day), mestranol (0.05–0.15 mg/day), and conjugated estrogenic hormones such as Premarin® (Wyeth-Ayerst; 0.2–2.5 mg/day). As used herein, the term "progestin" includes compounds having progestational activity such as, for example, progesterone, norethynodrel, norgestrel, megestrol acetate, norethindrone, progestin-based agents, and the like. Progestin-based agents include, for example, medroxyprogesterone such as Provera® (Upjohn; 2.5–10 mg/day), norethylnodrel (1.0–10.0 mg/day), and norethindrone (0.5–2.0 mg/day). A preferred estrogen-based compound is Premarin®, and norethylnodrel and norethindrone are preferred progestin-based agents. The method of administration of each estrogen- and progestin-based agent is consistent with that known in the art.

The formulations which follow are given for purposes of illustration and are not intended to be limiting in any way. The total active ingredients in such formulations comprises from 0.1% to 99.9% by weight of the formulation. The term "active ingredient" means a compound of formula I.

Formulation 1: Gelatin Capsules

| Ingredient | Quantity (mg/capsule) |
| --- | --- |
| Active Ingredient | 0.1–1000 |
| Starch NF | 0–500 |
| Starch flowable powder | 0–500 |
| Silicone fluid 350 centistokes | 0–15 |

The ingredients are blended, passed through a No. 45 mesh U.S. sieve, and filled into hard gelatin capsules.

Formulation 2: Tablets

| Ingredient | Quantity (mg/tablet) |
| --- | --- |
| Active Ingredient | 2.5–1000 |
| Starch | 10–50 |
| Cellulose, microcrystalline | 10–20 |
| Polyvinylpyrrolidone (as 10% solution in water) | 5 |
| Sodium carboxymethylcellulose | 5 |
| Magnesium stearate | 1 |
| Talc | 1–5 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules thus produced are dried at 50–60° C. and passed through a No. 18 mesh U.S. sieve. The sodium carboxymethylcellulose, magnesium stearate, and talc, previously passed through a No. 60 mesh U.S. sieve, are added to the above granules and thoroughly mixed. The resultant material is compressed in a tablet forming machine to yield the tablets.

Formulation 3: Aerosol

| Ingredient | Weight % |
| --- | --- |
| Active Ingredient | 0.25 |
| Ethanol | 29.75 |
| Propellant 22 | 70.00 |
| (Chlorodifluoromethane) | |
| Total | 100.00 |

The active ingredient is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4: Suppositories

| Ingredient | Weight |
| --- | --- |
| Active ingredient | 150 mg |
| Saturated fatty acid glycerides | 3000 mg |

The active ingredient is passed through a No. 60 mesh U.S. sieve and suspended in the fatty acid glycerides which had previously heated to their melting point. The mixture is poured into a suppository mold and allowed to cool.

Formulation 5: Suspension

Suspensions each containing 0.1–1000 mg of a compound of formula I per 5 mL dose.

| Ingredient | Weight |
| --- | --- |
| Active Ingredient | 0.1–1000 mg |
| Sodium carboxymethyl cellulose | 50 mg |
| Syrup | 1.25 mL |
| Benzoic acid solution (0.1M) | 0.10 mL |
| Flavor | q.v. |
| Color | q.v. |
| Purified water to total | Total 5 mL |

A compound of formula I is passed through a No. 45 mesh U.S. sieve and mixed with the sodium carboxymethyl cellulose and syrup to form a smooth paste. The benzoic acid solution, flavor, and color diluted in water are added and mixture stirred thoroughly. Additional water is added to bring the formulation to final volume.

The following examples and preparations are provided to better elucidate the practice of the present invention and should not be interpreted in any way as to limit the scope of same. Those skilled in the art will recognize that various modifications may be made while not departing from the spirit and scope of the invention. All publications and patent applications mentioned in the specification are indicative of the level of those skilled in the art to which this invention pertains.

EXAMPLES

NMR data for the following Examples were generated on a GE 300 MHz NMR instrument, and anhydrous d-6 DMSO was used as the solvent unless otherwise indicated.

Preparation 1

3,4-Dihydro-1-(4-methoxybenzoyl)]-6-methoxy-2-naphthalenyl diphenyl phosphoric acid ester

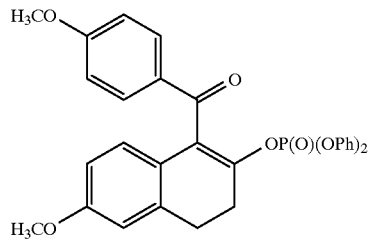

To a solution of 3,4-Dihydro-6-methoxy-1-(4-methoxybenzoyl)-2(1H)-naphthalenone (1.50 g, 0.0048 mol) at 5° C. under N₂ in 15 mL CH₂Cl₂ was added diphenylchlorophosphate (1.36 g, 0.0051 mol) and 4-dimethylaminopyridine (5 mg). Triethylamine (0.514 g, 0.0051 mol) in CH₂Cl₂ (20 mL) as then added dropwise over 10 min, while keeping the reaction temperature below 5° C. The resulting mixture was stirred overnight, and then it was poured over brine and ice and the crude product was extracted by EtOAc (50 mL). The organic layer was washed with brine, dried over anhydrous K₂CO₃, and evaporated to obtain 2.92 g of a yellow oil. Silica gel chromatography which utilized 10% EtOAc in toluene gave the desired product as a yellow oil, 2.17 g (83%) This material gave a strong peak in its field desorption mass spectrum at M/e 542 and was essentially a single component by NMR spectroscopy. However, it failed to crystallize and did not give an acceptable combustion analysis for carbon.

Anal. (C₃₁H₂₇PO₇) calcd C, 68.63; H, 5.02; O, 12.96. Found: C, 65.37; H, 4.89; O, 13.26.

¹H NMR (CDCl₃) δ 7.91 (d, J=8.8 Hz, 2H), 7.20–6.97 (m, 9H), 6.95–6.73 (m, 5H), 6.58 (dd, J=8.5 Hz, J=2.4 Hz, 1H), 3.83 (s, 3H), 3.75 (s, 3H), 3.07 (t, J=7.8 Hz, 2H), 2.88 (t, J=7.8 Hz, 2H); MS (FD) m/e 542 (M+).

Preparation 2

[3,4-Dihydro-6-methoxy-2-(3-methoxyphenyl)-1-naphthalenyl](4-methoxyphenyl)methanone

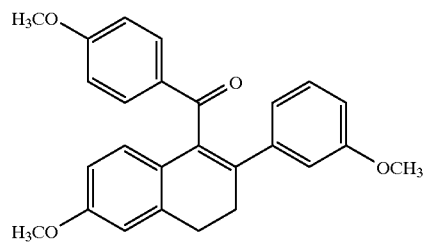

Sodium hydride (60% in mineral oil, 5.4 g, 0.135 mol) was suspended in anhydrous THF (80 mL) under a nitrogen atmosphere and the mixture was cooled to 5° C. in an ice bath. A solution containing 3,4-dihydro-6-methoxy-1-(4-methoxybenzoyl)-2(1H)-naphthalenone (38.0 g, 0.122 mol) and diphenyl chlorophosphate (36.3 g, 28.0 mL, 0.135 mol) in THF (150 mL) was added at a rate so that the temperature of the reaction mixture remained below 10° C. Following the initially rapid evolution of hydrogen gas, the reaction mixture was stirred for 2 hr with continued cooling from the ice bath. Analysis of a small sample by TLC (SiO₂, Toluene:EtOAc, 9:1) showed essentially quantitative formation of the enolphosphate intermediate. The reaction mixture was maintained near 0° C. and 3-methoxyphenyl magnesium bromide (250 mL of a 0.74 M solution in THF, 0.185 mol) was added by cannula over approximately 5 min. The resulting mixture was stirred at 0° C. for 2 hour, and then it was allowed to warm to 25° C. overnight. By TLC analysis, loss of enolphosphate had accompanied the formation of a major product, which migrated at high Rf. The reaction was worked up by pouring it over a large excess of iced NH₄Cl solution, and the crude product was extracted with ethyl acetate. The organic extracts were washed with brine and dried over anhydrous sodium sulfate. After filtration and removal of the solvents, a brown oil was obtained. The oil was purified by chromatography over silica gel, which employed a hexane to chloroform gradient. Pooling and concentration of appropriate fractions gave an amber oil which amounted to 40.3 g (83%).

¹H NMR (CDCl₃) δ 7.85 (d, J=8.6 Hz, 2H)7.10–7.0 (m, 1H), 6.90–6.70 (m, 6H), 6.70–6.60 (m, 2H), 3.80 (s, 6H), 3.67 (s, 3H), 3.10–2.90 (m, 2H), 2.90–2.70 (m, 2H); MS (FD) m/e 400 (M+); Anal. Calc'd. for C₂₆H₂₄O₄: C, 77.98; H, 6,04; N, 0.00. Found: C, 77.49; H, 6.20; N, 0.00.

Preparation 3

3,4-dihydro-1-[4-[2-(1-piperidinyl) ethoxy] benzoyl)]-6-methoxy-2-naphthalenyl diphenyl phosphoric acid ester

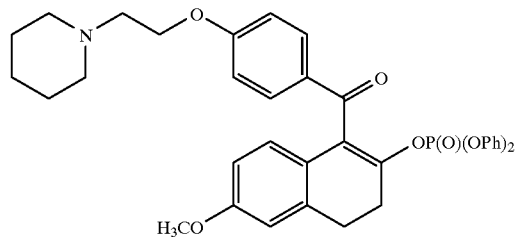

In a manner similar to that used in Preparation 1, the title compound was prepared as a yellow oil.

¹H NMR (CDCl₃) δ 7.85 (d, J=8.7 Hz, 2H), 7.39–6.92 (m, 9H), 6.92–6.69 (m, 5H), 6.57 (dd, J=8.5 Hz, J=2.4 Hz, 1H), 4.03 (t, J=5.9 Hz, 2H), 3.77 (s, 3H), 3.07 (t, J=8.1 Hz, 2H), 2.89 (t, J=8.1 Hz, 2H),2.78 (t, J=7.2, 2H), 2.62–2.42 (m, 4H), 1.77–1.55 (m, 4H), 1.55–1.37 (m, 2H); MS (FD) m/e 639 (M+).

EXAMPLE 1

[3,4-Dihydro-6-methoxy-2-(3-[3,4-dihydro-6-methoxy-2-(3-methoxyphenyl)-1-naphthalenyl][4-[2-(1-piperidinyl)ethoxy]phenyl]methanone hydrochloride

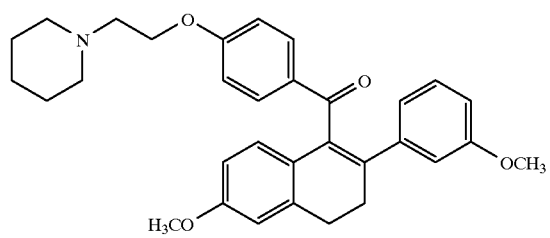

Sodium hydride (60% in mineral oil, 2.68 g, 0.067 mol) was suspended in anhydrous THF (300 mL) under a nitrogen atmosphere and the suspension was cooled to 5° C. in an ice bath. A solution consisting of 3,4-dihydro-1-[4-[2-(1-piperidinyl)ethoxy]benzoyl)]-6-methoxy-2-naphthalenyl diphenyl phosphoric acid ester (26.0 g, 0.0638 mol) in a minimum of THF was added dropwise. After the evolution of hydrogen subsided, the mixture was kept cooled and stirred for an hour to complete formation of the enolate. With continued cooling, diphenyl chlorophosphate (17.1 g, 13.2 mL, 0.0638 mol) in THF (75 mL) was added at a rate so that the temperature of the reaction mixture remained below 10° C. Following the completion of the addition, the reaction mixture was allowed to warm to room temperature while stirring was continued. Analysis of a small sample by TLC (SiO₂, Toluene:EtOAc, 9:1) showed essentially quantitative formation of the enol phosphate intermediate. The reaction mixture was maintained near 5° C. and 3-methoxyphenyl magnesium bromide (150 mL of a 0.64 M solution in THF, 0.096 mol) was added by cannula. The resulting mixture was stirred at 0° C. for 1 hour, and then it was allowed to warm to 250° C. and stirred for one hour longer. The reaction was kept cool and carefully quenched by gradual addition of 50 mL of 1N sulfuric acid. After adjusting the pH to 7.0, most of the THF was removed under reduced pressure. The aqueous residue was distributed between water and chloroform. The organic layer was washed with brine and dried over anhydrous sodium sulfate. Concentration provided an oil which was purified by chromatography over silica gel which utilized a gradient from chloroform to chloroform:methanol (95:5) to elute the product. Appropriate fractions provided 36 g of the crude free base which was practically identical to the free base product of Example 2. The free base was dissolved in methanol and treated with an excess of 5N HCl solution, then concentrated to dryness. The residue was recrystallized from methanol-ethyl acetate to provide 27.8 g (82%) of the desired hydrochloride salt: $^1$H NMR (DMSO-$d_6$) δ 10.09 (bs, 1H), 7.76 (d, J=8.7 Hz, 1H), 7.11–7.02 (m, 2H), 6.94 (d, J=8.8 Hz, 1H), 6.86 (d, J=1.2 Hz, 1H), 6.81–6.72 (m, 2H), 6.66 (dd, J=8.2 Hz, 2.5, 1H), 6.61 (d, J=3.1 Hz, 1H), 4.37 (t, J=4.6 Hz, 2H), 3.69 (s, 3H), 3.57 (s, 3H), 3.01–2.82 (m, 4H), 2.78–2.63(m, 2H), 1.81–1.58 (m, 5H), 1.31 (m, 1H); MS (FD) m/e 497 (M+; loss of HCl); Anal. Calc'd. for Anal. Calc'd. for $C_{32}H_{36}ClNO_4$: C, 71.96; H, 6.79; N, 2.62. Found: C, 71.69; H, 6.77; N, 2.48.

Preparation 4

[6-Methoxy-2-(3-methoxyphenyl)-1-naphthalenyl](4-methoxyphenyl)methanone

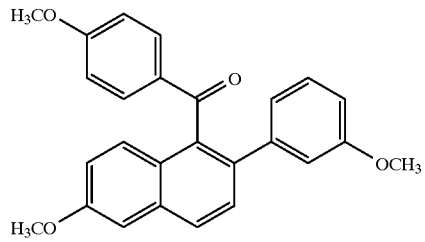

A solution of [3,4-dihydro-6-methoxy-2-(3-methoxyphenyl)-1-naphthalenyl](4-methoxyphenyl)methanone (14.0 g, 35.0 mmol) was dissolved in anhydrous dioxane (400 mL) under an atmosphere of nitrogen. 2,3-dichloro-5,6-dicyano-1,4-benzoquinone (DDQ, 7.0 g, 31 mmol) was added and the solution was refluxed for 16 hours. The reaction mixture was allowed to cool to ambient temperature and the solid dihydroquinone byproduct (8.8 gm) was removed by filtration and discarded. The filtrate was concentrated to dryness and the residue was purified by silica gel chromatography with chloroform as the isocratic elution solvent. Appropriate fractions gave 13.1 g, (94%) of the desired product as an oil. Although the oil contained some minor impurities, it was used without additional purification. $^1$H NMR (CDCl$_3$) δ 7.88 (d, J=8.6 Hz, 1H), 7.71–7.54 (m, 4H), 7.21 (d, J=2.6 Hz, 1H), 7.18–7.05 (m, 2H), 6.99–6.89 (m, 2H), 6.78–6.70 (m, 3H), 3.94 (s, 3H), 3.78 (s,3H), 3.69 (s,3H); MS (FD) m/e 398 (M+); Anal. Calcd. for $C_{26}H_{22}O_4$: C, 78.37; H, 5.57. Found: C, 78.22; H, 5.83.

Preparation 5

[3,4-Dihydro-6-methoxy-2-(3-methoxyphenyl)-1-naphthalenyl](4-hydroxyphenyl)methanone

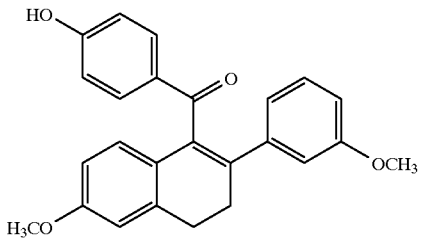

To EtSH (12.5 g, 14.9 mL. 0.20 mol) in anhydrous ethyl ether (300 mL) at −78° C. under a dry nitrogen atmosphere in a 1 L single neck RB flask was added slowly via syringe 1.6M n-BuLi (113 mL, 0.180 mol) over 1 hour. After addition was complete, the ether was removed under vacuum and a solution of [3,4-dihydro-6-methoxy-2-(3-methoxyphenyl)-1-naphthalenyl](4-methoxyphenyl)methanone, (24.0 g, 0.065 mol) in anhydrous DMF (150 mL) was added. The reaction mixture was heated at 70–80° C. for 2.5 hours and then at 65° C. for 20 hr. TLC analysis (SiO$_2$, Toluene:EtOAc, 9:1) showed the starting material to be nearly gone. Two spots were present at lower $R_f$. These were attributed to the desired product and the corresponding diphenol (lowest spot). The reaction mixture was allowed to cool and was then poured into 500 mL iced 1N HCl solution. The crude product was extracted into EtOAc. The EtOAc phase was washed with saturated aqueous NaCl solution, dried over anhydrous MgSO$_4$, and evaporated to a yellow oil. The product was purified by chromatography over silica gel using a gradient consisting of chloroform changing linearly to (95:5) chloroform:methanol. Following evaporation of the appropriate fractions, a yellow oil was obtained which was recrystallized from ethyl ether to yield 21.3 g, (54%) of the desired product, mp 197–8° C.

$^1$H NMR (CDCl$_3$) δ 7.76 (d, J=8.6 Hz, 2H), 7.10–7.00 (m, 1H), 6.90–6.70 (m, 4H), 6.70–6.60 (m, 4H), 6.07 (bs, 1H), 3.78 (s, 3H), 3.62 (s, 3H), 3.10–2.90 (m, 2H), 2.90–2.70 (m, 21H); MS (FD) m/e 386 (M+); Anal. Calc'd. for $C_{25}H_{22}O_4$: C, 77.70; H, 5.74. Found: C, 77.45; H, 5.66.

Preparation 6

[6-Methoxy-2-(3-methoxyphenyl)-1-naphthalenyl](4-hydroxyphenyl)methanone

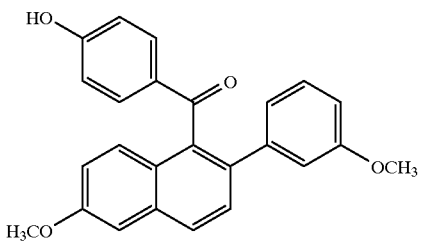

The above compound was prepared in an analogous manner as in Preparation 5. The title compound was isolated as a tan solid, 6.3 g (50%), mp 158–9° C.

$^1$H NMR (CDCl$_3$) δ7.86 (d, J=8.4 Hz, 1H), 7.63–7.49 (m, 4H), 7.20 (d, J=2.6 Hz, 1H), 7.15–7.05 (m, 2H), 6.95–6.86

(m, 2H), 6.70 (d, J=8.0 Hz, 1H), 6.61 (d, J=8.8 Hz, 2H), 6.32 (bs, 1H), 3.93 (s, 3H), 3.63 (s, 3H); MS (FD) m/e 384 (M+); Anal. Calcd. for $C_{25}H_{20}O_4$: C, 78.11; H, 5.24. Found: C, 78.36; H, 5.27.

EXAMPLE 2

[3,4-Dihydro-6-methoxy-2-(3-[3,4-dihydro-6-methoxy-2-(3-methoxyphenyl)-1-naphthalenyl][4-[2-(1-piperidinyl)ethoxy]phenyl]methanone (Alternate Synthesis)

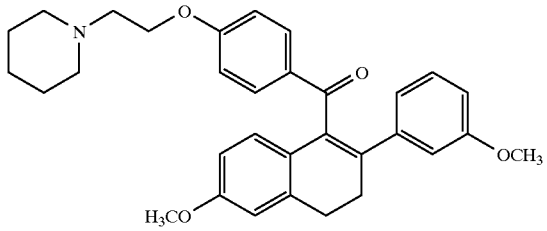

Compound [3,4-dihydro-6-methoxy-2-(3-methoxyphenyl)-1-naphthalenyl](4-hydroxyphenyl) methanone, (3.5 g, 9.0 mmol), anhydrous $K_2CO_3$ (6.25 g, 45 mmol), N-2-chloroethylpiperidine hydrochloride (1.75 g, 9.5 mmol, Aldrich Chem. Co.) 10 mg of KI, and anhydrous DMF (150 mL) were combined under a nitrogen atmosphere and the resulting mixture was stirred at room temperature for 16 hr. The DMF was removed under reduced pressure and the residue was distributed into water and ethyl acetate. The organic layer was separated, washed with brine and dried over anhydrous sodium sulfate. After concentration to an oil, the product was purified by column chromatography over silica gel using a gradient from chloroform to 95:5 chloroform:methanol. The appropriate fractions gave, on evaporation of the solvent and vacuum drying of the residue at 80° C. overnight, an oil which weighed 3.1 g. (69%).

$^1$H NMR (CDCl$_3$) δ 7.80 (d, J=9.0 Hz, 2H), 7.10–7.00 (m, 1H), 6.90–6.70 (m, 6H), 6.70–6.68 (m, 2H), 4.09 (t, J=5.9 Hz, 2H), 3.78 (s, 3H), 3.65 (s, 3H), 3.02 (t, J=8.1 Hz, 2H), 2.90–2.70 (m, 4H), 2.60–2.40 (m, 3H), 1.70–1.50 (m, 5H), 1.50–1.01 (m, 2H); MS (FD) m/e 497 (M+); Anal. Calc'd. for $C_{32}H_{35}NO_4$: C, 77.24; H, 7.09; N, 2.82. Found: C, 77.05; H, 7.19; N, 3.05.

EXAMPLE 3

[6-Methoxy-2-(3-methoxyphenyl)-1-naphthalenyl] [4-[2-(1-piperidinyl)ethoxy]phenylmethanone] hydrochloride

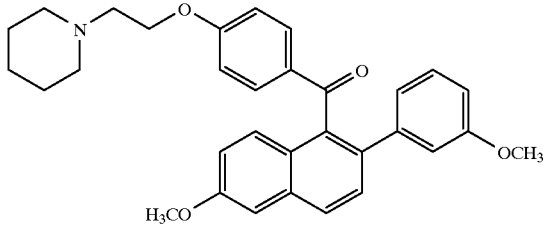

The above compound was prepared in an analogous manner to that of Example 2, and isolated as the hydrochloride salt. White solid, 6.95 g (80%), mp 91–2° C.

$^1$H NMR (DMSO-d$_6$) δ 10.24 (bs, 1H), 8.01 (d, J=8.6 Hz, 1H), 7.61–7.52 (m, 4H), 7.46 (d, J=2.4 Hz, 1H), 7.20–7.11 (m, 2H), 6.97–6.81 (m, 4H), 6.76 (dd, J=8.6, J=2.4, 1H), 4.41–4.31 (m, 2H), 3.87 (s, 3H), 3.61 (s, 3H), 3.52–3.33 (m, 4H), 3.01–2.80 (m, 2H), 1.80–1.58 (m, 5H), 1.31 (m, 1H),; MS (FD) m/e 496 (MH+ of free base); Anal. Calc'd. for $C_{32}H_{34}ClNO_4$: C, 72.24; H, 6.44; N, 2.63. Found: C, 72.53; H, 6.56; N, 2.66.

EXAMPLE 4

[3,4-Dihydro-6-hydroxy-2-(3-methoxyphenyl)-1-naphthalenyl][4-[2-(1-piperidinyl)ethoxy] phenylmethanone]

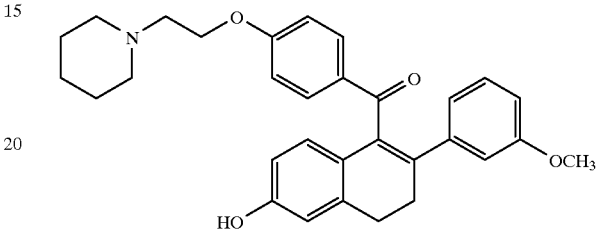

To EtSH (1.86 g, 2.21 mL. 0.03 mol) in anhydrous ethyl ether (30 mL) at −70° C. under a dry nitrogen atmosphere in a 200 mL single neck RB flask was added slowly via syringe 1.6M n-BuLi (12.5 mL, 0.02 mol). After addition was complete, the ether was removed under vacuum and a solution of [3,4-dihydro-6-methoxy-2-(3-methoxyphenyl)-1-naphthalenyl][4-[2-(1-piperidinyl)ethoxy] phenylmethanone]hydrochloride (1.07 g, 0.002 mol) in anhydrous DMF (30 mL) was added. The reaction mixture was heated in a 105° C. oil bath for 3 hours. TLC analysis (SiO2, chloroform:methanol, 9:1) showed the starting material to be nearly gone. Numerous spots were present at higher, as well as lower R$_f$. The spots lower than starting material were attributed to the desired product and the corresponding monophenolic species. The reaction mixture was allowed to cool somewhat and most of the DMF was removed under reduced pressure. The residue was distributed between brine (300 mL) which contained 5 g ammonium chloride and ethyl acetate (100 mL). The aqueous phase was separated and extracted with 3 25 mL portions of ethyl acetate. The combined ethyl acetate extracts were washed with 4 10 mL portions of brine, dried over anhydrous magnesium sulfate, and concentrated to provide 1.31 g. of a brown foul-smelling oil. The oil was purified (in two portions) by radial chromatography over silica gel with an elution gradient consisting of 2.5% methanol in chloroform and changing gradually to 40% of methanol. The product eluted slightly slower than the starting material. Following combination and concentration of the appropriate fractions, 338 mg (35%) of the desired material was obtained. In order to improve the purity, the material was re-chromatographed, which provided 272 mg (28%) of essentially pure material.

$^1$H NMR (DMSO-d$_6$) d 9.56 (s, 1H), 7.75 (d, J=8.8 Hz, 2H), 7.14–7.08 (m, 1H), 6.92 (d, J=8.8 Hz, 2H), 6.82–6.75 (m, 2H), 6.73–6.65 (m, 2H), 4.08 (t, J=5.8 Hz, 2H), 3.34 (s, 3H), 2.90 (t, J=7.3 Hz, 2H), 2.76–2.65 (m, 2H), 2.61 (t, J=5.7 Hz, 2H), 2.52–2.48 (m, 2H), 2.45–2.28 (m, 3H), 1.54–1.41 (m, 3H), 1.40–1.29 (m, 2H); MS (FD) m/e 483 (MH+).

The following discussions illustrate methods of use for the compounds of formula I in experimental models or in clinical studies. These examples are for the purposes of illustration and are not meant to be limiting in any way.

A. Osteoporosis:

Experimental models of postmenopausal osteoporosis are known in the art. Germane to this invention is the ovariectomized rat model which is provided in U.S. Pat. No. 5,393,763. The compounds of formula I would be active in this model and would demonstrate an effective treatment or prevention of bone loss due to the deprivation of estrogen.

An additional demonstration of the method of treating or preventing osteoporosis due to estrogen deprivation would be as follows: One hundred patients would be chosen, who are healthy postmenopausal women, aged 45–60 and who would normally be considered candidates for estrogen replacement therapy. This includes women with an intact uterus, who have had a last menstrual period more than six months, but less than six years. Patients excluded for the study would be those who have taken estrogens, progestins, or corticosteroids six months prior to the study or who have ever taken bis-phosphonates.

Fifty women (test group) would receive 15–80 mg of a compound of formula I, for example, Formulation 1 (above), per day. The other fifty women (control group) would receive a matched placebo per day. Both groups would receive calcium carbonate tablets (648 mg) per day. The study is a double-blind design. Neither the investigators nor the patients would know to which group each patient is assigned.

A baseline examination of each patient includes quantitative measurement of urinary calcium, creatinine, hydroxyproline, and pyridinoline crosslinks. Blood samples are measured for serum levels of osteocalcin and bone-specific alkaline phosphatase. Baseline measurements would also include a uterine examination and bone mineral density determination by photon absorptiometry.

The study would continue for six months, and each the patients would be examined for changes in the above parameters. During the course of treatment, the patients in the treatment group would show a decreased change in the biochemical markers of bone resorption as compared to the control group. Also, the treatment group would show little or no decrease in bone mineral density compared to the control group. Both groups would have similar uterine histology, indicating the compounds of formula I have little or no uterotrophic effects.

B. Hyperlipidemia:

Experimental models of postmenopausal hyperlipidemia are known in the art. Germane to this invention is the ovariectomized rat model which is detailed in U.S. Pat. No. 5,464,845. Data presented in Table 1 show comparative results among ovariectomized rats, rats treated with 17-a-ethynyl estradiol ($EE_2$), and rats treated with certain compounds of this invention. Although $EE_2$ caused a decrease in serum cholesterol when orally administered at 0.1 mg/kg/day, it also exerted a stimulatory effect on the uterus so that $EE_2$ uterine weight was substantially greater than the uterine weight of the ovariectomized animals. This uterine response to estrogen is well recognized in the art.

Not only did the compounds of the present invention reduce serum cholesterol compared to the ovariectomized animals, but the uterine weight was increased to lesser extent than those given $EE_2$. Compared to estrogenic compounds known in the art, the benefit of serum cholesterol reduction while lessening the effect on uterine weight is unusual and desirable.

As expressed in the data below, estrogenicity also was assessed by evaluating the response of eosinophil infiltration into the uterus. The compounds of this invention did not cause as large an increase in the number of eosinophils observed in the stromal layer of the ovariectomized, rat uteri. $EE_2$ caused a substantial and expected increase in eosinophil infiltration.

The data presented in Table 1 reflect the response per treatment group.

TABLE

| Compound δ | Dose mg/kg[a] | Uterine Wt. (% Inc.)[b] | Uterine EPO (Vmax)[c] | Serum Cholesterol (% Dec.)[δ] |
|---|---|---|---|---|
| $EE_2$[e] | 0.1 | 200.2* | 276.5* | 98.6* |
| Ex. 2 (1st Experiment) | 0.1 | −26.5* | 16.7 | 76.6* |
|  | 1 | −11.2 | 21.5 | 70.3* |
|  | 10 | −22.6 | 6.5 | 64.0 |
| Ex. 2 (2nδ Experiment) | 0.01 | −12.8 | 2.0 | 15.1 |
|  | 0.1 | 18.3 | 11.3 | 50.5 |
|  | 1 | −11.8 | 6.5 | 63.5* |
| Example 3 | 0.1 | 18.6 | 3.9 | 34.1* |
|  | 1.0 | 45.9* | 6.0 | 66.0* |
|  | 10 | 23.9* | 4.8 | 61.6* |

[a]mg/kg PO
[b]Uterine Weight % increase versus the ovariectomized controls
[c]Eosinophil peroxidase, $V_{max}$
[d]Serum cholesterol decrease versus ovariectomized controls
[e]17-α-Ethynyl-estradiol An additional demonstration of the method of treating hyperlipidemia due to estrogen deprivation would be as follows: One hundred patients would be chosen, who are healthy postmenopausal women, aged 45–60, and who would normally be considered candidates for estrogen replacement therapy. This would include women with an intact uterus, who have not had a menstrual period for more than six months, but less than six years. Patients excluded for the study would be those who have taken estrogens, progestins, or corticosteroids.

Fifty women (test group) would receive 15–80 mg of a compound of formula I, for example, using Formulation 1, per day. The other fifty women (control group) would receive a matched placebo per day. The study would be a double-blind design. Neither the investigators nor the patients would know to which group each patient is assigned.

A baseline examination of each patient would include serum determination of cholesterol and tri-glyceride levels. At the end of the study period (six months), each patient would have their serum lipid profile taken. Analysis of the data would confirm a lowering of the serum lipids, for example, cholesterol and/or tri-glycerides, in the test group versus the control.

We claim:

1. A compound of formula I

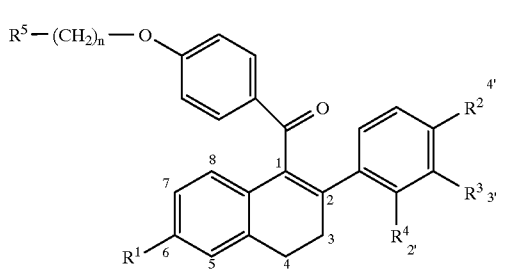

wherein $R^1$ is —H, —OH, —O($C_1$–$C_4$ alkyl), —OCO($C_1$–$C_6$ alkyl), —O—CO—O($C_1$–$C_6$ alkyl), —O—CO—Ar, —OSO$_2$(C$_2$–C$_6$ alkyl), —O—CO—OAr, where Ar is optionally substituted phenyl;

R$^2$ is —H, —Cl, —F, C$_1$–C$_4$ alkyl, —OH, —O(C$_1$–C$_4$ alkyl), —OCO(C$_1$–C$_6$ alkyl), —O—CO—O(C$_1$–C$_6$ alkyl), —O—CO—Ar, —OSO$_2$(C$_2$–C$_6$ alkyl), or —O—CO—OAr, where Ar is optionally substituted phenyl;

R$^3$ and R$^4$ are, independently, R$^2$, with the proviso that R$^3$ and R$^4$ are not both hydrogen and with the further proviso that at least one of R$^1$, R$^2$, R$^3$, and R$^4$ must be —O—CO—O(C$_1$–C$_6$ alkyl), —OSO$_2$(C$_2$–C$_6$ alkyl), or —O—CO—OAr;

R$^5$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino; and n is 2 or 3;

or a pharmaceutically acceptable salt or solvate thereof.

2. A compound according to claim 1 wherein R$^3$ is methoxy.

3. A compound according to claim 2 wherein R$^1$ is hydroxy.

4. A compound according to claim 1 wherein n is two.

5. A compound according to claim 1 wherein R$^5$ is piperidinyl.

6. A pharmaceutical formulation comprising a compound according to claim 1 in combination with a pharmaceutically acceptable carrier, diluent, or excipient.

7. A method for inhibiting bone loss or bone resorption comprising administering to a patient in need of such treatment an effective amount of a compound of claim 1, or a pharmaceutically acceptable salt or solvate thereof.

8. The method according to claim 7 wherein said bone loss or bone resorption is due to menopause or ovariectomy.

9. A method of lowering serum cholesterol comprising administering to a patient in need thereof an effective amount of a compound of claim 1, or a pharmaceutically acceptable salt or solvate thereof.

* * * * *